United States Patent [19]

Lim et al.

[11] Patent Number: 5,672,180
[45] Date of Patent: Sep. 30, 1997

[54] STORAGE STABLE 2-METHYL-1-NAPHTHOL COUPLERS

[75] Inventors: Mu-Ill Lim, Trumbull; Yuh-Guo Pan, Stamford; Linas R. Stasaitis, Fairfield, all of Conn.; John D. O'Donoghue, Rye Brook, N.Y.

[73] Assignee: Clairol Incorporated, New York, N.Y.

[21] Appl. No.: 632,224

[22] Filed: Apr. 15, 1996

Related U.S. Application Data

[63] Continuation of Ser. No. 527,911, Sep. 14, 1995, Pat. No. 5,529,583.
[51] Int. Cl.$^6$ .................................................. A61K 7/13
[52] U.S. Cl. .................................... 8/408; 8/406; 8/424
[58] Field of Search ................................ 8/406, 408, 424, 8/649, 613, 604, 435

[56] References Cited

U.S. PATENT DOCUMENTS

| | | | |
|---|---|---|---|
| 2,001,992 | 5/1935 | Wagner et al. | 8/424 |
| 2,162,458 | 6/1939 | Lehmann | 8/424 |
| 3,770,442 | 11/1973 | Meyer et al. | 96/82 |
| 4,508,810 | 4/1985 | Wartman | 430/201 |
| 5,344,463 | 9/1994 | Chan et al. | 8/408 |

FOREIGN PATENT DOCUMENTS

| | | |
|---|---|---|
| 2915736 | 11/1980 | Germany. |
| 62-35262 | 2/1987 | Japan. |
| 1-19029 | 1/1989 | Japan. |

OTHER PUBLICATIONS

English language translation of JP 62–35262, Konishiroku Shashin Kogyo, pp. 1–25 Feb. 1987.

*Primary Examiner*—Paul Lieberman
*Assistant Examiner*—Caroline L. Dusheck
*Attorney, Agent, or Firm*—Morton S. Simon

[57] ABSTRACT

Compounds of Formula II

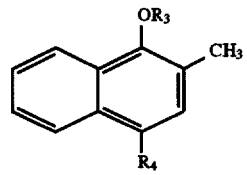

wherein $R_3$ is —COOCH$_3$, —COCH$_3$ or —COCH$_2$CH$_3$ and $R_4$ is hydrogen or $R_3$ is hydrogen and $R_4$ is —OCH$_3$, —OCH$_2$CH$_3$, —OCH$_2$CH$_2$OH or —OCH$_2$CH$_2$OCH$_3$ are storage stable and can be used in oxidative hairdye systems in place of the storage unstable 2-methyl-1-naphthol. Advantageously, it has been found to produce the same colors as 2-methyl-1-naphthol.

10 Claims, No Drawings

STORAGE STABLE 2-METHYL-1-NAPHTHOL COUPLERS

This is a continuing application of application Ser. No. 08/527,911 filed Sep. 14, 1995, now U.S. Pat. No. 5,529,583.

BACKGROUND OF THE INVENTION

U.S. Pat. No. 5,344,463 discloses hair dye compositions and methods utilizing as couplers 2-substituted-1-naphthol compounds of the Formula I, or salts thereof,

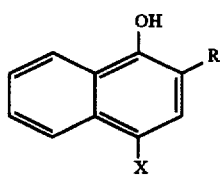

I wherein X is hydrogen or halogen; R is $C_1$–$C_6$ alkyl, hydroxy $C_1$–$C_6$ alkyl, amino $C_1$–$C_6$ alkyl, wherein the amino group is substituted by $R^1$ and $R^2$ with $R^1$ and $R^2$ being, independently, hydrogen, $C_1$–$C_6$ alkyl, hydroxy $C_1$–$C_6$ alkyl, or $R^1$ and $R^2$ taken together with the nitrogen atom to which they are attached form a 5 or 6 membered saturated ring or an olefinic group selected from the group consisting of ethylene, propylene and butylene.

1-naphthol has been used in hair dye compositions for many years. It has proven to have long term storage stability. One skilled in the art would expect the 2-substituted-1-naphthol compounds of U.S. Pat. No. 5,344,463 to likewise have long term storage stability. The present inventors have surprisingly and unexpectedly found that such is not the case.

2-Methyl-1-naphthol decomposes upon standing at room temperature, in air. Within several weeks it changes from a white crystalline compound to a dark liquid. The decomposition was confirmed by HPLC analysis. It might be expected that the instability is related to the electron density of the substrate. The more electron dense the substrate, the greater the instability of the 2-methyl-1-naphthol. However, this was not found to be the case. Several of the 2-methyl-1-naphthols of U.S. Pat. No. 5,344,463 are more storage stable than 2-methyl-1-naphthol even though they are more electron rich. Moreover, 2-methyl-1-trifluoroacetoxynaphthalene is storage unstable, despite the fact that it is more electron deficient than 2-methyl-1-naphthol.

4-Halogenated derivatives of 2-methyl-1-naphthol might be expected to be more storage stable than the parent compound. However, the 4-halogenated derivatives proved an unsatisfactory solution because of their lower solubility in hair dye bases. Moreover, since the halogen weight is lost during dye formation, only a fraction of the weight is useful and dye formation is hindered due to the resultant lower electron density.

OBJECT OF THE INVENTION

It is an object of the present invention to produce storage stable 2-methyl-1-naphthols of U.S. Pat. No. 5,344,463, thereby making them more useful in preparing hair dye compositions.

DESCRIPTION OF THE INVENTION

As noted earlier, it is surprising and unexpected that 2-methyl-1-naphthol is unstable at room temperature, in air. Since 2-methyl-1-trifluoroacetoxynaphthalene also decomposes upon exposure to air at room temperature, one skilled in the art would expect that other derivatives of 2-methyl-1-naphthol would likewise be unstable at room temperature and in air. Surprisingly and unexpectedly, the present inventors have discovered that certain derivatives of the 2-methyl-1-naphthols of U.S. Pat. No. 5,344,463 are stable upon storage at room temperature and exposure to air.

The novel derivatives of the present invention conform to the general Formula II

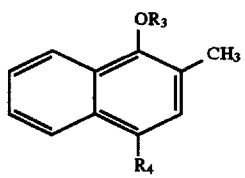

II wherein $R_3$ is —COOCH$_3$, —COCH$_3$ or —COCH$_2$CH$_3$ and $R_4$ is hydrogen (this subgrouping will be referred to as IIa

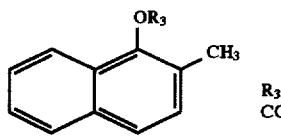

IIa $R_3$ = COOCH$_3$, COCH$_3$ or COCH$_2$CH$_3$), or $R_3$ is hydrogen and $R_4$ is —OCH$_3$, —OCH$_2$CH$_3$, —OCH$_2$CH$_2$OH or —OCH$_2$CH$_2$OCH$_3$ (this subgrouping will be referred to as IIb

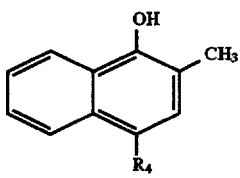

IIb $R_4$ = OCH$_3$, OCH$_2$CH$_3$, OCH$_2$CH$_2$OH, OCH$_2$CH$_2$OCH$_3$).

The novel compounds of formula II offer improved storage stability. Moreover, they can be employed in hair dye compositions without any complication. Still further, they advantageously dye hair the same color as is obtained through use of 2-methyl-1-naphthol.

The compounds of formula IIa would be far less useful if it were necessary to perform a separate chemical reaction on them before they could be employed in hair dye preparations. But this is not the case, surprisingly, these compounds are readily hydrolyzed by standard alkaline hair dye bases which utilize monoethanolamine, aminomethylpropanol or ammonia as the alkali and which are produced and maintained at ambient temperature. It is surprising that this is the case since the hydrolysis of aromatic acetates generally requires elevated temperature and strong acids (in this regard attention is directed U.S. Pat. No. 3,194,734, col. 5, line 54 et seq) or the use of stronger nucleophiles (see U.S. Pat. No. 4,054,413, column 4, line 4 et seq). Moreover, it is not even necessary that the compounds of formula IIa be hydrolyzed by the hair dye base alone. The compounds of formula IIa are very quickly hydrolyzed when a hair dye base containing a compound of formula IIa is mixed with hydrogen peroxide.

The following examples are offered to illustrate the present invention.

EXAMPLE 1

Preparation of 2-methyl-1-naphthalenol methylcarbonate

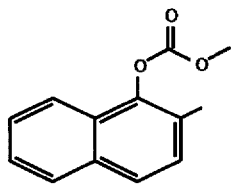

2.64 g (26 mmole) of triethylamine were added to a stirred solution of 3.16 g (20 mmole) of 2-methyl-1-naphthol in 25 mL of ethyl acetate, while the solution was maintained in an ice bath. Then 2.36 g (25 mmole) methyl chloroformate were added portionwise to the solution. The reaction mixture was stirred for one hour and then 100 mL diethylether was added. The reaction mixture was filtered over a Celite pad and the filtrate concentrated to give 3.65 g (85% yield) of an oil which was crystallized in hexane. The resulting crystals had a melting point of 54°–55° C. The following $^1$HNMR was obtained: (300 MHz, DMSO-$d_6$) δ2.30 (s, 3H), 3.89 (s, 3H), 7.44 (d, 1H, J=8 Hz), 7.48–7.58 (m, 2H), 7.78 (t, 2H, J=9 Hz), 7.95 (d, 1H, J=8 Hz). The mass spectrum showed a molecular ion at m/z 216.

EXAMPLE 2

Preparation of 2-methyl-1-(2'2'2'-trifluoroacetoxy) naphthalene

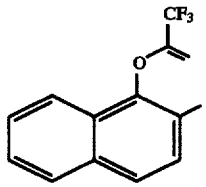

2.64 g (26 mmole) of triethylamine was added, with stirring, to a solution of 3.16 g (20 mmole) of 2-methyl-1-naphthol in 25 mL of ethyl acetate, while the solution was maintained in an ice bath. Then 5.25 g (25 mmole) of trifluoroacetic anhydride was added portionwise. The reaction mixture was stirred for one hour, washed with water three times, dried over anhydrous sodium sulfate, then evaporated to give an oil. Crystallization of the oil in hexane yielded 850 mg (17% yield) of the title compound having a melting point of 34° C. and an $^1$HNMR analysis as follows: (300 MHz, DMSO-$d_6$) δ2.31 (s, 3H), 7.51 (d, 1H, J=8 Hz), 7.54–7.65 (m, 2H), 7.82 (d, 1H,J=8 Hz), 7.91 (d, 1H, J=8 Hz), 8.00 (d, 1H, J=8 Hz). The mass spectrum showed a molecular ion at m/z 254.

EXAMPLE 3

Preparation of 4-methoxy-2-methyl-1-naphthol

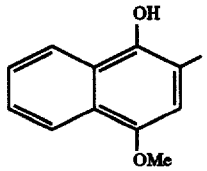

4.9 g of concentrated sulfuric acid were added dropwise to a stirred mixture of 4.75 g (27.6 mmole) of 2-methyl-1, 4-naphthoquinone, 2.71 g (41.4 mmole) of zinc powder, 15 mL of methanol and 15 mL of toluene, in an ice bath. After the addition was complete, the reaction mixture was stirred for 4.5 hours at 60° C. The reaction product was extracted with ethyl acetate, washed with water then brine, dried over sodium sulfate, filtered, then evaporated under reduced pressure to yield 4.25 gm (81% yield) of the title compound as an off-white powder having a melting point of 102°–103° C. and an $^1$HNMR as follows: (300 MHz, DMSO-$d_6$) δ2.38 (s, 3H), 3.91 (s, 3H), 6.76 (s, 1H), 7.42(m, 2H), 8.04 (d, 1H, J=8.1 Hz), 8.14 (d, 1H, J=8.1 Hz), 8.50(bs, 1H). The mass spectrum showed a molecular ion at m/z 188.

EXAMPLE 4

Preparation of 4-(2'-hydroxyethoxy)-2-methyl-1-hydroxynaphthalene

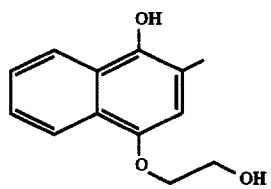

4.9 g of concentrated sulfuric acid were added dropwise, with stirring, to a mixture of 4.75 g (27.6 mmole) 2-methyl-1,4naphthoquinone, 2.71 g (41.4 mmole) of zinc powder, 15 mL of ethylene glycol and 15 mL of toluene in an ice bath. After the addition was complete, the reaction mixture was stirred for 5 hours at 100° C. The reaction product was extracted with ethyl acetate, washed with water, brine, dried over sodium sulfate, filtered, then evaporated under reduced pressure to give 4.21 g (70% yield) of the above product. That product had a melting point of 136.3°–136.8° C. and an $^1$HNMR as follows: (300 MHz, DMSO-$d_6$) δ2.37 (s, 3H), 3.86 (m, 2H), 4.10 (t, 2H, J=4.8 Hz), 4.98 (t, 1H, J=5.4 Hz), 6.76 (s, 1H), 7.42 (m, 2H), 8.14 (d, 1H, J=9.0 Hz), 8.17 (d, 1H, J=9.0 Hz), 8.51 (s, 1H). The mass spectrum showed a molecular ion at m/z 218.

EXAMPLE 5

Preparation of 4-(2'-methoxyethoxy)-2-methyl-1-naphthol

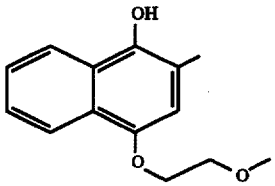

4.9 g of concentrated sulfuric acid were added dropwise, with stirring, to a mixture of 4.75 g (27.6 mmole) of 2-methyl-1,4-naphthoquinone, 2.71 g (41.4 mmole) of zinc powder, 15 mL of 2-methoxyethanol and 15 mL of toluene, in an ice bath. After the addition was completed, the reaction mixture was stirred for 5 hours at 100° C. The reaction product was extracted with ethyl acetate, washed with water, then brine, dried over sodium sulfate, filtered, then evaporated under reduced pressure to give 4.87 g (76% yield) of the title compound. The resultant product had a melting point of 100°–101° C. and an $^1$HNMR as follows: (300 MHz, DMSO-$d_6$) δ2.33 (s, 3H), 3.34 (s, 3H), 3.79 (t, 2H, J=4.5 Hz), 4.21 (t, 2H, J=4.5 Hz), 6.78(s, 1H), 7.47 (m, 2H), 8.08 (d, 1H, J=8.0 Hz), 8.14 (d, 1H, J=8.0 Hz), 8.54 (s, 1H). The mass spectrum showed a molecular ion at m/z 232.

EXAMPLE 6

Preparation of 1-acetoxy-2-methylnaphthalene.

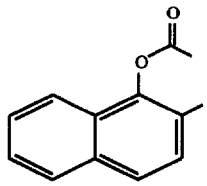

A solution of 9.48 g (60 mmole) of 2-methyl-1-naphthol and 8.10 g (80 mmole) of triethylamine in 50 mL of ethyl acetate was cooled to below 5° C. in an ice-bath. 5.50 g (70 mmole) of acetyl chloride was added at a rate such that the temperature did not rise about 5° C. The reaction mixture was stirred for an additional one hour, diluted with 50 mL of ethyl acetate, and washed with water then brine. The organic layer was dried over anhydrous sodium sulfate, filtered and evaporated to give an oily residue. Crystallization in hexane yielded 7.58 g (63% yield) of the title compound with a melting point of 81°–83° C. and an $^1$HNMR as follows: (300 MHz, DMSO-$d_6$) δ2.26 (s, 3H), 2.48 (s, 3H), 7.42 (d, 1H, J=9 Hz), 7.46–7.55 (m, 2H), 7.47–7.81 (m, 2H), 7.92 (d, 1H, J=9 Hz). The mass spectrum showed a molecular ion at m/z 200.

EXAMPLE 7

Preparation of 2-methyl-1-naphthalenol propionate

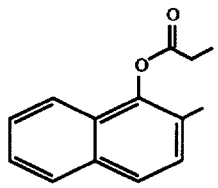

A solution of 3.16 g (20 mole) of 2-methyl-1-naphthol and 2.64 g (26 mmole) of triethylamine in 25 mL of ethyl acetate was cooled to below 5° C. in an ice-bath. 2.31 g (25 mmole) of propionyl chloride were added at a rate such that the temperature did not rise above 5° C. The reaction mixture was stirred for an additional one hour and diluted with 100 mL of diethyl ether. The reaction mixture was filtered through a Celite pad and the filtrate was concentrated to give 3.75 g (87% yield) of an oil. The oil was crystallized in hexane to give the title compound with a melting point of 50°–51° C. and a $^1$HNMR spectrum: (300 MHz, DMSO-$d_6$) δ1.23 (t, 3H J=8 Hz), 2.24 (s, 3H), 2.84 (q, 2H, J=8 Hz), 7.42 (d, 2H, J=9 Hz), 7.46–7.54 (m, 2H), 7.75 (d, 1H, J=9 Hz) 7.92 (d, 1H, j=9 Hz). The mass spectrum showed a molecular ion at m/z 214.

To demonstrate the storage stability of the compounds of the present invention, test samples of the title compounds of Examples 1, 2, 3, 4, 5 and 6 were placed in clear glass vials and kept on top of a laboratory desk for the time indicated. Samples of 2-methyl-1-naphthol, 1-naphthol and phenyl trifluoroacetate used as controls were similarly kept. One sample of 2-methyl-1-naphthol was stored under nitrogen and in a dry ice chest (temperature of approximately –50° C.). A second sample of 2-methyl-1-naphthol and the remaining test samples were stored at room temperature.

Methanol solutions of the samples were periodically prepared and analyzed by HPLC on a Zorbax ODS Column, with methanol/water as the mobile phase. Purity of the main peak was determined by a Diode Array detector. The test results are reported in Table 1 which follows. It should be appreciated that the test has a margin of error of 1%. Thus, reported values which differ by 1% or less should be considered as not different.

It is evident from the results in Table 1, particularly by comparison to phenyl trifluoroacetate, that the instability of 2-methyl-1-(2'2'2'-trifluoroacetoxy)-naphthalene arises from the 2-methyl-1-naphthol moiety. Although 2-methyl-1-naphthol can be used, if stored at –50° C. and under nitrogen, this is impractical. It is surprising and unexpected that replacing 2-methyl-1-naphthol by a compound of formula II of the present invention affords results comparable to 2-methyl-1-naphthol stored at –50° C. and under nitrogen. If one examines the impurity content (100% -purity), it is evident that compounds of formula II of the present invention afford a 20 fold reduction in the impurities obtained through the use of 2-methyl-1-naphthol stored at room temperature in air. The commercial value of using the compounds of formula II, in lieu of 2-methyl-1-naphthol, in oxidative hair dye compositions is self evident.

TABLE 1

Stability of 2-Methyl-1-Napthol Derivatives

| Compound/Comments | Time after synthesis/Percentage Purity | | | |
|---|---|---|---|---|
| 2-methyl-1-naphthalenol methylcarbonate (Example 1) | +56 days/ /99.8% | +71 days/ /98.3% | +85 days/ /98.1% | +113 days/ /98.4% |
| 2-methyl-1-(2'2'2'-trifluoroacetoxy)naphthalene (Example 2) | | | | |
| (a) room temp./air | | +95 days /0% | | |
| (b) –10° C. | +24 days/ 85.6% | +95 days/ 76.4% | | |
| 4-methoxy-2-methyl-1-naphthol (Example 3) | +82 days/ /96.6% | +97 days/ /96.6% | +111 days/ /96.3% | +139 days/ /97.0% |
| 4-(2'-hydroxyethoxy)-2-methyl-1-hydroxy-naphthalene (Example 4) | +75 days/ /97.7% | +90 days/ /97.7% | +104 days/ /96.3% | +132days/ /97.1% |
| 4-(2'-methoxyethoxy)-2- | +72 days/ | +87 days/ | +101 days/ | +129 days/ |

TABLE 1-continued

Stability of 2-Methyl-1-Napthol Derivatives

| Compound/ Comments | Time after synthesis/Percentage Purity | | | |
|---|---|---|---|---|
| methyl-1-naphthol (Example 5) | /97.1% | /97.0% | /96.0% | /97.1% |
| 1-acetoxy-2-methyl-naphthalene (Example 6) | +23 days/ /97.6% | +38 days/ /97.7% | +52 days/ /96.6% | +80 days/ /97.2% |
| 2 methyl-1-naphthol | | | | |
| (a) room temp./air | +22 days/ /90.6% | +37 days/ /53.6% | +51 days/ /44.6% | |
| (b) −50° C./N$_2$ | +48 days/ /96.9% | +77 days/ /97.3% | +105 days/ /97.8% | |
| 1-naphthol | minimum 90 days/ 98.6% | +14 days/ /98.2% | +42 days/ /98.5% | |
| phenyl trifluoroacetate | minimum 90 days/ 97.6% | | | |

Dye compositions employing compounds of formula II of the present invention may be formulated as a solution, a liquid shampoo (which can be a solution or an emulsion), a cream, a gel, a powder, or an aerosol.

Primary intermediates, other couplers and semipermanent dyes known to be useful in compositions for dyeing hair on a living human head may be utilized with compounds of the present invention. Such components are described in various papers such as "Hair Colouring" by J. F. Corbett (Review of the Progress of Coloration, Volume 15, pages 52–65, (1985)) and "Oxidative Dyeing of Keratin Fibers" by K. C. Brown, S. Pohl, A. E. Kezer and D. Cohen (Journal of the Society of Cosmetic Chemists, Volume 36, pages 31–37, (1985)). Examples of primary intermediates include, but are not limited to, the following: p-phenylenediamine 2,5-diaminotoluene, 2,5-diaminoanisole, 2-chloro-p-phenylenediamine N-phenyl-p-phenylenediamine, N,N-bis-(2'-hydroxyethyl)-p-phenylenediamine, 2-methyl-N1-(2'-hydroxyethyl)-p-phenylenediamine, p-aminophenol, N-methyl-p-aminophenol, 4-amino-m-cresol, 2,4,5,6-tetraaminopyrimidine, 2,4-diaminophenol, benzene-1,2,4-triol, toluene-2,4,5-triol. Other couplers which may be used with the present invention include, but are not limited to, the following: resorcinol, 4-chlororesorcinol, 2-methylresorcinol, pyrogallol, pyrocatechol, hydroquinone, 1-naphthol, naphthalene-1,5-diol, naphthalene-1,7-diol, 5-hydroxybenzodioxane, 2,5-dihydroxy-4-methylpyridine, m-amino-phenol, o-aminophenol, 5-amino-2-methylphenol, 5-(β-hydroxyethylamino)-2-methylphenol, 6-hydroxybenzomorpholine, m-phenylenediamine, 3,3'-dihydroxydiphenylamine, 2,6-diaminopyridine. Examples of the semipermanent dyes are: N-(2'-hydroxyethyl)-o-nitroaniline, 4-nitro-o-phenylenediamine, N1-(2'-hydroxyethyl)-4-nitro-o-phenylenediamine, N1-tris-(hydroxymethyl)methyl-4-nitro-o-phenylenediamine, 2-amino-3-nitrophenol, 2-amino-4-nitrophenol, 4-amino-2-nitrophenol, 2-amino-5-nitrophenol, O,N-bis-(2'-hydroxyethyl)-2-amino-5-nitrophenol, N-(2'-hydroxyethyl)-2-amino-5-nitroanisole, 4-amino-3-nitrophenol, N-(2'-hydroxyethyl)-4-amino-3-nitrophenol, N-(2'-hydroxyethyl)-4-amino-3-nitroanisole, 1-(3-methylamino-4-nitrophenoxy)propane-2,3-diol, 3-methylamino-4-nitrophenoxyethanol, 2-nitro-p-phenyl-enediamine, N1-(2'-hydroxyethyl)-2-nitro-p-phenylenediamine, N4-(2'-hydroxyethyl)-2-nitro-p-phenylenediamine, N1-methyl-2-nitro-p-phenylenediamine, N1,N4,N4-tris(2'-hydroxyethyl)-2-nitro-p-phenylenediamine, N4-(2'-hydroxyethyl)-N1,N4-dimethyl-2-nitro-p-phenylenediamine, N4-(2',3'-dihydroxypropyl)-N1,N4-dimethyl-2-nitro-p-phenylenediamine, 4-nitro-m-phenylenediamine, picramic acid, N-methyl-isopicramic acid, 4-amino-2-nitrodiphenylamine, 4-hydroxy-2'-nitrodiphenylamine, 4-(p-aminophenylazo)-N,N-bis(2'-hydroxy-ethyl)aniline, 1,4,5,8-tetraaminoanthraquinone, 1,4-diaminoanthraquinone, 1-amino-4-methylaminoanthraquinone, 1-(2'-hydroxyethylamino)-4-methylaminoanthraquinone, and 2,4-diamino-2'-hydroxy-5'-nitroazobenzene-5-sulphonic acid (Na salt).

Materials typically included in hair dye compositions and/or developers include, for example, organic solvents and solubilizing agents, surface active agents, thickening agents, buffers, chelating agents, perfumes, sunscreens, conditioners, dyeing assistants or penetrating agents, preservatives, emulsifiers and fragrances. A particular material may perform several functions. For example, a surfactant may also act as a thickener.

It is often advantageous to include in the dye compositions of the present invention an organic solvent or solvent system which helps solubilize the dyes and adjuvants contained in the compositions. A number of organic solvents are known for such purpose. These include: alcohols, particularly alkyl alcohols of 1–6 carbons, especially ethanol and propanol; glycols of up to about 10 carbons, preferably less than 6 carbons, especially propylene glycol and butylene glycol; glycol ethers of up to about 10 carbons, especially diethyleneglycol monobutyl ether; carbitols; and benzyl alcohol. When present, the solvents will constitute from about 1% to about 60%, preferably from about 10% to about 30%, by weight of the dyeing composition.

Typical surfactant types useful in the compositions of the invention include: alkyl sulfates, alkyl ether sulfates, amide ether sulfates, soaps, alkyl ether carboxylates, acylsarcosinates, protein/fatty acid condensates, sulfosuccinic acid esters, alkane sulfonates, alkylbenzene sulfonates, α-olefin sulfonates, acylisethionates, acyltaurines, ethoxylates, sorbitan esters, alkanolamides, amine oxides, quaternary ammonium salts, alkyl betaines, amidopropyl betaines, sulfobetaines, glycinates/aminopropionates and carboxyglycinates/aminodipropionates. A combination of different surfactants can be used to impart particular viscosity and foaming properties.

Illustrative of specific surfactants that may be employed are: lauryl sulfate; polyoxyethylene lauryl ester; myristyl sulfate; glyceryl monostearate; sodium salt of palmitic acid, methyl taurine; cetyl pyridinium chloride; lauryl sulfonate; myristyl sulfonate; lauric diethanolamide; polyoxyethylene stearate; stearyl dimethyl benzyl ammonium chloride: dodecyl benzene sodium sulfonate; nonyl naphthalene sodium sulfonate; dioctyl sodium sulfosuccinate; sodium N-methyl-N-oleyl taurate; oleic acid ester of sodium isethionate; sodium dodecyl sulfate, and the like. The quantity of water soluble surface active agent employed can vary widely up to about 15%. Preferably, the surface active agent is employed in an amount of from about 0.10% to about 10%, based on the weight of the composition.

The thickening agent, when employed, may be one or a mixture of those commonly used in hair dyeing compositions or in hair developers. Such thickening agents include: sodium alginate; gum arabic; cellulose derivatives, such as methylcellulose or the sodium salt of carboxymethylcellulose; acrylic polymers, such as polyacrylic acid sodium salt; and inorganic thickeners, e.g., bentonite and fumed silica. Electrolytes, alkanolamides, cellulose ethers and highly ethoxylated compounds (such as ethers, esters and diesters) may also be used to thicken the composition. The quantity of thickening agent can vary over a wide range. Typically, the thickening agent(s) is employed in an amount of up to about 20%, more preferably, from about 0.1% to 5%, based on the weight of the composition.

The pH of the dye composition can vary from about 2.5 to about 11. Any compatible water dispersible alkalizing agent can be incorporated in the composition in an amount suitable to give the desired pH. Typically, the amount of alkalizing agent employed is less than about 10%, preferably, from about 0.1% to about 5%, based on the weight of the composition. Preferred alkalizing agents are monoethanolamine, aminomethylpropanol and ammonia. However, mono-, di- and trialkanolamines, alkyl amines and heterocyclic amines may be used; examples of these are triethanolamine, 2-amino-2-methyl-1,3-propanediol, diethylamine, dipropylamine, morpholine, piperidine, 2-pipecoline and piperazine.

Any inorganic or organic acid or acid salt, that is compatible with the dye composition and does not introduce toxicity under its conditions of use, can also be employed to adjust the pH of the dye composition. Illustrative of such acids and acid salts are sulfuric acid, formic acid, acetic acid, lactic acid, citric acid, tartaric acid, ammonium sulfate, sodium dihydrogen phosphate, and potassium bisulfate.

Common chelating agents that can be employed in the compositions of the invention include the salts of ethylenediaminetetraacetic acid (EDTA), nitrilotriacetic acid, phosphates, pyrophosphates and zeolites.

Conditioners that can be incorporated in the present compositions include: encapsulated silicones; silicones, such as amino functional and carboxy silicones; volatile silicones; combinations of a cationic polymer, a decomposition derivative of keratin and a salt; quaternary ammonium compounds such as cocos($C_{12-18}$)-alkyl poly(6)oxyethyl di-(2-lauroyloxyethyl)-methyl ammonium chloride; combinations of a plant extract and a polypeptide; a dimethyl diallyl ammonium chloride (DMDAAC)/acrylic acid type polymer; and a dialkyl quaternary ammonium compound where the alkyl groups are $C_{12}$-$C_{16}$. Other well known conditioners, such as lanolin, glycerol, oleyl alcohol, cetyl alcohol, mineral oil and petrolatum, can also be incorporated.

It is a common practice to add solvents or swelling agents to enhance the penetration of hair dyes. Materials useful for swelling hair include acetic acid, formic acid, formamide, urea, ethyl amine and certain alkali halides (potassium iodide, sodium bromide, lithium bromide and lithium chloride, but not sodium chloride). N-Alkyl pyrrolidones and epoxy pyrrolidone may be employed to potentially increase the penetration of dye into hair. Imidazolines such as disclosed in U.S. Pat. No. 5,030,629 may be employed in the compositions to enhance the penetration of hair dyes.

Emulsifiers may be used when the final form of the hair dye is an emulsion. Many emulsifiers are by their nature also surfactants. There are five general categories: anionic, cationic, nonionic, fatty acid esters and sorbitan fatty acid esters. Examples include: mono-, dialkyl and trialkyl ether phosphates, long-chain fatty acids with hydrophilic compounds such as glycerin, polyglycerin or sorbitol and long chain alkyl primary and secondary amines, quaternary ammonium and quaternary pyridinium compounds.

Materials which may render the product aesthetically more appealing, such as fragrances, proteins hydrolysates, vitamins and plant extracts, may be added. Examples include chamomile, aloe vera, ginseng, and pro-vitamin B.

What is claimed is:

1. In an oxidative dye system for dyeing a keratin fiber wherein an oxidant is reacted with a composition containing a primary intermediate, a coupler or a coupler precursor, and a cosmetically acceptable vehicle therefor, the improvement which comprises the coupler or the coupler precursor is a compound having the formula IIa

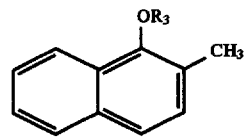

wherein $R_3$ is —COOCH$_3$, —COCH$_3$ or —COCH$_2$CH$_3$.

2. The system as claimed in claim 1, wherein $R_3$ is —COCH$_3$.

3. The system as claimed in claim 1, further including at least one material selected from the group consisting of perfumes, antioxidants, sequestering agents, acidifying agents, alkalizing agents, swelling agents and developers.

4. The system as claimed in claim 1, wherein the composition contains an alkalizing agent selected from the group consisting of monoethanolamine, aminomethylpropanol and ammonia and the oxidant is hydrogen peroxide.

5. In a method for producing an oxidative hair dye wherein a peroxide containing composition is mixed with an alkaline composition containing a primary intermediate and a coupler, the improvement comprising the coupler is a compound of formula IIb

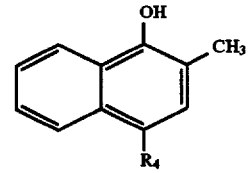

wherein $R_4$ is —OCH$_3$, —OCH$_2$CH$_3$, —OCH$_2$CH$_2$OH or —OCH$_2$CH$_2$OCH$_3$, the alkaline composition contains monoethanolamine or aminomethylpropanol as the alkalizing agent, and the alkaline composition is maintained at ambient temperature.

6. In a method for producing an oxidative hair dye wherein a peroxide containing composition is mixed with an alkaline composition containing a primary intermediate and a coupler precursor, the improvement comprising the coupler precursor is a compound of formula IIa

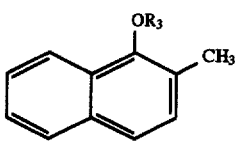

IIa wherein R₃ is —COOCH₃, —COCH₃ or —COCH₂CH₃, the alkaline composition contains monoethanolamine, aminomethylpropanol or ammonia as the alkalizing agent, and the alkaline composition is maintained at ambient temperature.

7. A method for reducing undesired by-products in an oxidative hair dye prepared by reacting an oxidant with an alkaline composition containing an alkali, a primary intermediate and a 2-methyl-1-naphthol derivative, said method comprising preparing said alkaline compositions by dissolving in an aqueous vehicle (i) an amount of a compound of formula IIa wherein R₃ is —COOCH₃, —COCH₃ or —COCH₂CH₃

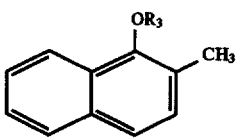

IIa (ii) said primary intermediate, and (iii) an alkali selected from the group consisting of monoethanolamine, aminomethylpropanol and ammonia; then mixing the alkaline composition with the oxidant to produce an indo dye that is identical to one that would be produced had the alkaline composition contained 2-methyl-1-naphthol rather than the compound of formula IIa wherein R₃ is —COOCH₃, —COCH₃ or —COCH₂CH₃.

8. A method for reducing undesired by-products in an oxidative hair dye prepared by reacting an oxidant with an alkaline composition containing an alkali, a primary intermediate and 2-methyl-1-naphthol substituted at the 4-position by —OCH₃, —OCH₂CH₃, —OCH₂CH₂OH or —OCH₂CH₂OCH₃, said method comprising preparing said alkaline composition by dissolving in an aqueous vehicle (i) an amount of a compound of formula IIb wherein R₄ is —OCH₃, —OCH₂CH₃,

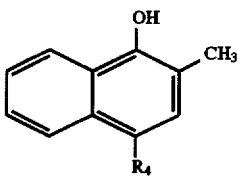

IIb

—OCH₂CH₂OH or —OCH₂CH₂OCH₃, (ii) said primary intermediate, and (iii) an alkali selected from the group consisting of monoethanolamine and aminomethylpropanol; then mixing the alkaline composition with the oxidant to produce an indo dye that is identical to one that would be produced had the alkaline composition contained 2-methyl-1-naphthol rather them the compound of formula IIb wherein R₄ is —OCH₃, —OCH₂CH₃, —OCH₂CH₂OH or —OCH₂CH₂OCH₃.

9. In an oxidative dye system for dyeing a keratin fiber wherein an oxidant is reacted with a composition containing a primary intermediate, a coupler or a coupler precursor, an alkalizing agent selected from the group consisting of monoethanolamine and aminomethylpropanol, and a cosmetically acceptable vehicle therefor, the improvement which comprises the coupler or the coupler precursor is a compound having the formula IIb

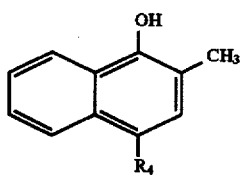

IIb wherein R₄ is —OCH₃, —OCH₂CH₃, —OCH₂CH₂OH or —OCH₂CH₂OCH₃.

10. The system as claimed in claim 9, further including at least one material selected from the group consisting of perfumes, antioxidants, sequestering agents, acidifying agents, swelling agents and developers.

* * * * *